United States Patent
Gleave et al.

(10) Patent No.: US 9,717,792 B2
(45) Date of Patent: Aug. 1, 2017

(54) COMBINATION THERAPY FOR CANCER USING HSP27 INHIBITOR AND EGFR TYROSINE KINASE INHIBITORS OR ANTI-FOLATES

(71) Applicant: The University Of British Columbia, Vancouver (CA)

(72) Inventors: Martin E. Gleave, Vancouver (CA); Amina Zoubeidi, Vancouver (CA); Masafumi Kumano, Kobe (JP)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 14/372,972

(22) PCT Filed: Feb. 1, 2013

(86) PCT No.: PCT/IB2013/050882
§ 371 (c)(1),
(2) Date: Jul. 17, 2014

(87) PCT Pub. No.: WO2013/114339
PCT Pub. Date: Aug. 8, 2013

(65) Prior Publication Data
US 2015/0050285 A1    Feb. 19, 2015

Related U.S. Application Data

(60) Provisional application No. 61/594,173, filed on Feb. 2, 2012.

(51) Int. Cl.

| | | |
|---|---|---|
| *C12N 15/113* | (2010.01) | |
| *A61K 31/7088* | (2006.01) | |
| *A61K 31/517* | (2006.01) | |
| *A61K 31/519* | (2006.01) | |
| *A61K 39/395* | (2006.01) | |
| *A61K 31/5377* | (2006.01) | |
| *A61K 31/713* | (2006.01) | |
| *A61K 39/00* | (2006.01) | |

(52) U.S. Cl.
CPC ........ *A61K 39/3955* (2013.01); *A61K 31/517* (2013.01); *A61K 31/519* (2013.01); *A61K 31/5377* (2013.01); *A61K 31/7088* (2013.01); *A61K 31/713* (2013.01); *C12N 15/113* (2013.01); *A61K 2039/505* (2013.01); *C12N 2310/11* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 7,087,613 | B2* | 8/2006 | Norris | A61K 31/517 514/266.4 |
| 7,101,991 | B2 | 9/2006 | Gleave et al. | |
| 7,723,312 | B2* | 5/2010 | Gleave | A61K 31/7125 514/44 R |
| 2003/0170891 | A1 | 9/2003 | McSwiggen | |
| 2004/0033543 | A1* | 2/2004 | Schwab | C07K 16/2863 435/7.23 |
| 2004/0127441 | A1 | 7/2004 | Gleave et al. | |
| 2005/0271747 | A1 | 12/2005 | Higgins et al. | |
| 2006/0003954 | A1 | 1/2006 | Nath et al. | |
| 2006/0040886 | A1* | 2/2006 | Gleave | A61K 31/7125 514/44 A |
| 2007/0003555 | A1 | 1/2007 | LeClair | |
| 2009/0118208 | A1 | 5/2009 | Liu et al. | |
| 2009/0142413 | A1 | 6/2009 | Allen et al. | |
| 2009/0264502 | A1 | 10/2009 | Bennett et al. | |
| 2009/0281166 | A1 | 11/2009 | Gleave et al. | |
| 2009/0292008 | A1 | 11/2009 | Gleave et al. | |
| 2011/0117110 | A1 | 5/2011 | Akamatsu et al. | |
| 2011/0118298 | A1* | 5/2011 | Fritz | G01N 33/57492 514/291 |
| 2011/0144185 | A1 | 6/2011 | Worm | |
| 2012/0022132 | A1 | 1/2012 | Sah et al. | |
| 2014/0351961 | A1* | 11/2014 | Asea | A61K 47/48246 800/8 |
| 2015/0232843 | A1* | 8/2015 | Gleave | C12N 15/113 514/44 A |

FOREIGN PATENT DOCUMENTS

| | | |
|---|---|---|
| EP | 0813872 A1 | 12/1997 |
| JP | 10036261 | 2/1998 |
| JP | 10036267 | 2/1998 |
| JP | 10045572 | 2/1998 |
| JP | 10045574 | 2/1998 |
| WO | 2004030660 A2 | 4/2004 |
| WO | 2007025229 A2 | 3/2007 |
| WO | 2007041294 A2 | 4/2007 |
| WO | 2012080509 A1 | 6/2012 |

OTHER PUBLICATIONS

Burris, HA (The Oncologist 2004 9(s3): 10-15).*
Okamoto, I. (FEBS J 2010 277: 309-315).*
Skvortsov et al. (Mol. Can. Therapeutics Dec. 2004, 3 (12): 1551-1558).*
Baselga J. (Euro. J. of Cancer 2001 37:s16-s22).*
Loeffler-Ragg (Euro. J. of Cancer 2005, 41:2338-2346).*
Halatsch et al. (J. Neurosurg. Aug. 2009 111: 211-217).*
Tannock, I.F. (Experimental Chemotherapy, Ch. 19—p. 338 and 352-359, in The Basic Science of Oncology Tannock and Hill, eds., New York 1992).*
Hotte et al., OGX-427, a 2'methoxyethyl antisense oligonucleotide (ASO), against HSP27: Results of a first-in-human trial, 2009, XP055167993, Retrieved from the Internet: URL:http://meetinglibrary.asco.org/print/585607 on Feb. 6, 2015.

(Continued)

*Primary Examiner* — Peter J Reddig
(74) *Attorney, Agent, or Firm* — Larson & Anderson, LLC

(57) ABSTRACT

Combination therapy for cancer makes use of HSP27 inhibitors and EGFR tyrosine kinase inhibitors or etiolates.

2 Claims, 10 Drawing Sheets

(56) References Cited

OTHER PUBLICATIONS

Tamm, I., Antisense therapy in malignant diseases: status quo and quo vadis?, Clinical Science, 2006, pp. 427-442, vol. 110, No. 4, XP055167727.

Baylot, V. et al., OGX-427 inhibits tumor progression and enhances gemcitabine chemothreapy in pancreatic cancer, Cell Death and Disease, 2011, p. e221, vol. 2, No. 10, XP055167621.

Supplementary European Search Report issued on Feb. 6, 2015 for corresponding European Patent Application No. 13744042.

Pectasides, D. et al., Testicular function in poor-risk nonseminomatous germ cell tumors treated with methotrexate, paclitaxel, ifosamide, and cisplatin combination chemotherapy, Journal of Andrology, 2009, pp. 280-286, vol. 30, No. 3.

Selvaggi. G. et al., Epidermal growth factor receptor overexpression correlates with a poor prognosis in completely resected non-small-cell lung cancer, Annals of Oncology, 2004, pp. 28-32, vol. 15.

Asthana A. et al, Homo sapiens heat shock 27kDa protein 3 (HSPB3), mRNA, NCBI Ref. Seq: NM_006308.2, May 3, 2014.

Hino, M. et al, Homo sapiens HSP27 mRNA, complete cds, GenBak: AB020027.1, Apr. 20, 2002.

Carper, S. W. et al., Human mRNA for heat shock protein HSP27, GenBank: X54079.1, Oct. 7, 2008.

Zhao, G.Y. et al., Homo sapiens heat shock 27kDA protein 1 (HSPB1), mRNA, NCBI Ref. Seq: NM_001540.3, May 25, 2014.

Prabhu, S. et al., Homo sapiens heat shock 27kDa protein 2 (HSPB2), mRNA, NCBI Ref. Seq: NM_001541.3, May 3, 2014.

Monari, M., et al., Heat shock protein beta-a [Canis lupus familiaris], NCBI Ref. Seq: NP_001003295.1, Apr. 26, 2014.

Zhang, Q., et al., Heat shock protein beta-1 [Bos taurus], NCBI Ref. Seq: NP_001020740.1, Jan. 24, 2014.

McGuire, VA., et al., Heat shock protein beta1 [Mus musculus], NCBI Ref. Seq. NP_038588.2, May 24, 2014.

Crosby, J. R. et al., Inhaled CD86 Antisense Oligonucleotide Suppresses Pulmonary Inflammation and Airway Hyper-Responsiveness in Allergic Mice, The Journal of Pharmacology and Experimental Therapeutics, 2007, pp. 938-946, vol. 321, No. 3.

Shin, K. D., et al. Blocking Tumor Cell Migration and Invasion with Biphenyl Isoxazole Derivative KRIBB3, a Synthetic Molecule That Inhibits Hsp27 Phosphorylation, The Journal of Biological Chemistry, 2005, pp. 41439-41448., vol. 280, No. 50.

Pao, W. et al., Acquired Resistance of Lung Adenocarcinomas to Gefitinib or Erlotinib is Associated with a Second Mutation in the EGFR Kinase Domain, PLoS Medicine, 2005, pp. 225-235, vol. 2, Issue 3, e73.

Van Schaeybroeck, S. et al., Chemotherapy-induced epidermal growth factor receptor activation determines response to combined gefitinib/chemotherapy treatment in non-small cell lung cancer cells, Mol Cancer Ther, 2006, pp. 1154-1165, vol. 5, No. 5, Downloaded from mct.aacrjournals.org on Jun. 26, 2014.

Horman, S. et al., Anti-Sense Inhibition of Small-Heat-Shock-Protein (HSP27) Expression in MCF-7 Mammary-Carcinoma Cells Induces Their Spontaneous Acquisition of a Secretory Phenotype, Int. J. Cancer, 1999, pp. 574-582, vol. 82.

Davey, H. M. et al., Flow Cytometry and Cell Sorting of Heterogeneous Microbial Populations: The Importance of Single-Cell Analyses, Microbiological Reviews, 1996, pp. 641-696, vol. 60, No. 4.

Chou, T-C, et al., Generalized Equations for the Analysis of Inhibitions of Michaelis-Menten and Higher-Order Kinetic Systems with Two or More Mutually Exclusive and Nonexclusive Inhibitors, Eur. J. Biochem, 1981, pp. 207-216, vol. 115.

Chou, T-C, et al. A Simple Generalized Equation for the Analysis of Multiple Inhibitions of Michaelis-Menten Kinetic Systems*, The Journal of Biological Chemistry, 1977, pp. 6438-6442, vol. 252, No. 18.

Theriault, J. R., et al., Essential Role of the NH2-terminal WD/EPF Motif in the Phosphorylation-activated Protective Function of Mammalian Hsp27, The Journal of Biological Chemistry, 2004, pp. 23463-23471, vol. 279, No. 22.

Tezel, G. et al., The Mechanisms of hsp27 Antibody-Mediated Apoptosis in Retinal Neuronal Cells, The Journal of Neuroscience, 2000, pp. 3552-3562, vol. 10, No. 10.

Yonekura, N. et al., Interferon-γ downregulates Hsp27 expression and suppresses the negative regulation of cell death in oral squamous cell carcinoma lines, Cell Death and Differentiation, 2003, pp. 313-322, vol. 10.

Morino, M. et al., Specific Regulation of HSPs in Human Tumor Cell Lines by Flavonoids, in vivo, 1997, pp. 265-270, XP009007378.

Bruey, JM, et al., Hsp27 negatively regulates cell death by interacting with cytochrome c, Nature Cell Biology, 2000, pp. 645-652, vol. 2.

Chauhan, D. et al., Blockade of Hsp27 Overcomes Bortezomib/Proteasome Inhibitor PS-341 Resistance in Lymphoma Cells, Cancer Research, 2003, pp. 6174-6177, vol. 63, Downloaded from cancerres.aacrjournals.org on Aug. 8, 2014.

Chou, TC et al., Analysis of combined drug effects: a new look at a very old problem, TIPS, 1983, pp. 450-454; Publisher: Elsevier Science Publishers B V, Amsterdam.

Concannon, C.G. et al., On the role of Hsp27 in regulating apoptosis, Apoptosis, 2003, pp. 61-70, vol. 8, Publisher: Kluwer Academic Publishers.

Giard, D. J. et al., In Vitro Cultivation of Human Tumors: Establishment of Cell Lines Derived From a Series of Solid Tumors, Journal of the National Cancer Institute, 1973, pp. 1417-1423, vol. 51, No. 5.

Gibert, B. et al., Inhibition of heat shock protein 27 (HspB1) tumorigenic functions by peptide aptamers, Oncogene, 2011, pp. 3672-3681, vol. 30.

Heinrich, J-C, et al., RP101 (brivudine) binds to heat shock protein HSP27 (HSPB1) and enhances survival in animals and pancreatic cancer patients, J Cancer Res Clin Oncol, 2011, pp. 1349-1361, vol. 137.

Karras, J. G. et al., Inhaled antisense oligonucleotide therapies: Inspiration and progress, Drug Discovery Today: Therapeutic Strategies, 2006, pp. 335-341, vol. 3, No. 3.

Lee, Y-J, et al., HSP25 Inhibits Protein Kinase Cδ-mediated Cell Death through Direct Interaction, The Journal of Biological Chemistry, 2005, pp. 18108-18119, vol. 280.

Tanaka, Y. et al., Paclitaxel inhibits expression of heat shock protein 27 in ovarian and uterine cancer cells, Int J Cynecol Cancer, 2004, pp. 616-620, vol. 14.

Rane, M. J. et al., Heat Shock Protein 27 Controls Apoptosis by Regulating Akt Activation*, The Journal of Biological Chemistry, 2003, pp. 27828-27835, vol. 278, No. 30.

Voss, O. H. et al., Binding of Caspase-3 Prodomain to Heat Shock Protein 27 Regulates Monocyte Apoptosis by Inhibiting Caspase-3 Proteolytic Activation, The Journal of Biological Chemistry, 2007, pp. 25088-25099, vol. 282, No. 34.

* cited by examiner

Fig. 5C
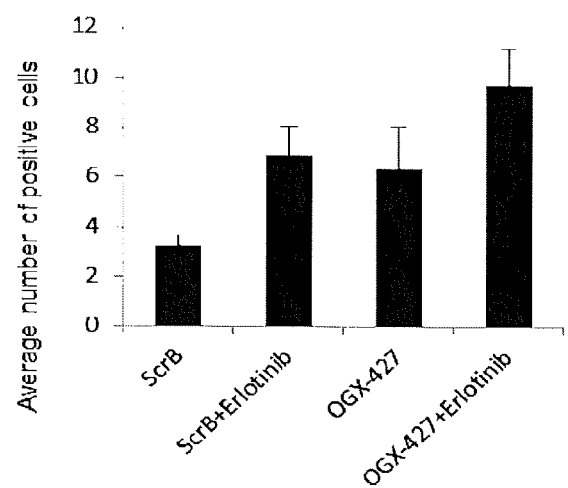
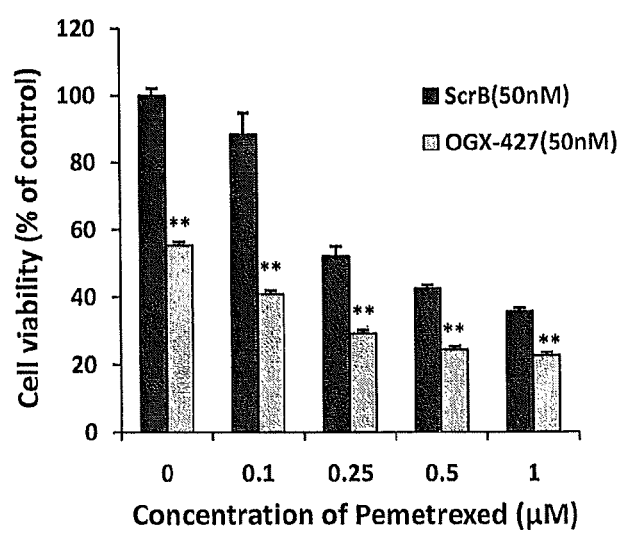
** P<0.01
Fig. 6

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: antisense of human hsp27
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (14)..(14)
<223> OTHER INFORMATION: m5c
<220> FEATURE:
<221> NAME/KEY: modified_base
<222> LOCATION: (17)..(17)
<223> OTHER INFORMATION: mo5u
<220> FEATURE:
<221> NAME/KEY: modified_base
<222> LOCATION: (18)..(18)
<223> OTHER INFORMATION: m5c
<220> FEATURE:
<221> NAME/KEY: modified_base
<222> LOCATION: (20)..(20)
<223> OTHER INFORMATION: mo5u

<400> SEQUENCE: 1
gggacgcggc gctcggucau                                                 20

<210> SEQ ID NO 2
<211> LENGTH: 19
<212> TYPE: RNA
<213> ORGANISM: homo sapiens
```

-continued

```
<400> SEQUENCE: 2
gcugcaaaau ccgau gaga                                              19

<210> SEQ ID NO 3
<211> LENGTH: 21
<212> TYPE: RNA
<213> ORGANISM: Artificial Sequence
<220> FEATURE:
<223> OTHER INFORMATION: scrambled control

<400> SEQUENCE: 3
cagcgcugac aacaguuuca  u                                           21
```

COMBINATION THERAPY FOR CANCER USING HSP27 INHIBITOR AND EGFR TYROSINE KINASE INHIBITORS OR ANTI-FOLATES

FIELD OF THE INVENTION

This application relates to combination therapy for the treatment of cancer using inhibitors of heat shock protein 27 (Hasp 27) and an epidermal growth factor tyrosine kinase inhibitor (EGFR-TKI) such as erlotinib, or antifolates such as pemetrexed.

BACKGROUND OF THE INVENTION

Hsp27 is a cell survival protein found at elevated levels in many human cancers including prostate, lung, breast, ovarian, bladder, renal, pancreatic, multiple myeloma and liver cancer. In addition, many anti-cancer therapies are known to further elevate Hsp27 levels. For example, Hsp27 levels increased four-fold in prostate cancer patients after treatment with chemo- or hormone therapy. Increased levels of Hsp27 in some human cancers are associated with metastases, poor prognosis and resistance to radiation or chemotherapy.

Hsp27 has been disclosed as a therapeutic target in the treatment of cancer. For example, U.S. Pat. No. 7,101,991 discloses antisense oligonucleotides and siRNA that inhibit Hsp27 expression. Additional oligonucleotide sequences targeting Hsp27 expression are disclosed in WO2007/025229 and US Patent Publications Nos. 2009/0264502 and 2011/0144185. Non-oligonucleotide compounds for inhibition of Hsp27 have also been disclosed, including berberine derivatives described in European Patent EP0813872, and compounds described in JP 10045572, JP 10045574, JP10036261 and JP 10036267, all assigned to Kureha Chemical Industries Co., Ltd. Paclitaxel has also been shown to be an inhibitor of Hsp27 expression. Tanaka et al., *Int J Gynecol Cancer.* 2004 July-August; 14(4):616-20. Nucleoside inhibitors that binds to Hsp27 are also known. One of these, bromovinyldeoxyuridine (BRDU, Brivudine, RP101) has been tested in clinical trials and shown to enhance survival of patients with pancreatic cancer. Tuukanen et al. J Cancer Res Clin Oncol. 2011 September; 137(9):1349-61.

Preclinical studies show that OGX-427, an antisense oligonucleotide described in U.S. Pat. No. 7,101,991 (Seq. ID No. 1, OncoGenex Technologies Inc.), significantly decreases levels of Hsp27, induces apoptosis in several human cancer cell lines, has single agent anti-tumor activity, and acts as a chemosensitizer in combination with several cytotoxic drugs including docetaxel. OGX-427 is being evaluated in a Phase 1 study in patients with breast, prostate, ovarian, non-small cell lung, or bladder cancer who have failed potentially curative treatments or for which a curative treatment does not exist.

SUMMARY OF THE INVENTION

The present inventors have discovered that combination therapy using Hsp27 inhibitors and EGFR tyrosine kinase inhibitors leads to superior therapeutic effects by reducing tumor growth rates and enhancing the cytotoxic effect of the EGFR tyrosine kinase inhibitors. Thus, in accordance with one aspect of the invention, a method is provided for treating cancer in an individual, including a human individual, comprising the steps of administering to the individual a therapeutically effective amount of a first active agent which is an inhibitor of Hsp27 activity, and administering to the individual a therapeutically effective amount of a second active agent which is an inhibitor of EGFR tyrosine kinase. The first and second agents are administered such that both are present at therapeutically relevant levels during a common time period. In some embodiments of the invention, treatment with the Hsp27 inhibitor is commenced prior to treatment with the EGFR tyrosine kinase inhibitor.

The present inventors have also discovered that combination therapy using Hsp27 inhibitors and an antifolate leads to superior therapeutic effects by reducing tumor growth rates and enhancing the cytotoxic effect of the antifolate. Thus, in accordance with one aspect of the invention, a method is provided for treating cancer in an individual, including a human individual, comprising the steps of administering to the individual a therapeutically effective amount of a first active agent which is an inhibitor of Hsp27 activity, and administering to the individual a therapeutically effective amount of a second active agent which is an antifolate. The first and second agents are administered such that both are present at therapeutically relevant levels during a common time period. In some embodiments of the invention, treatment with the Hsp27 inhibitor is commenced prior to treatment with the antifolate.

BRIEF DESCRIPTION OF THE DRAWINGS

FIG. 5C shows the average number of Tunel positive cells in cells treated with erlotinib, OGX-427 or both.

FIG. 6 shows cell viability as a function of pemetrexed treatment with and without treatment with Hsp27 antisense.

DETAILED DESCRIPTION OF THE INVENTION

Figure 1:
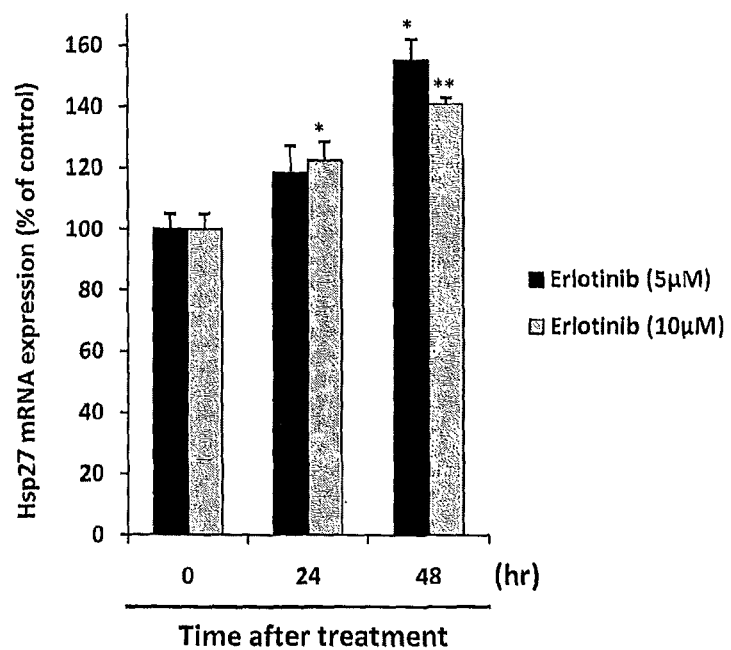
FIG. 1 shows induction of Hsp27 following treatment of A549 lung cancer cells with erlotinib.

The present invention provides a method for treating cancer in a patient diagnosed as suffering from cancer. In preferred embodiments, the patient is a human patient, although the method can also be used in veterinary applications, for example in the treatment of cancer in dogs, cats and other pets.

The occurrence of elevated levels of Hsp27 in various types of cancer and the demonstrated efficacy of Hsp27 inhibitors in multiple types of cancers is indicative of the general applicability of the present invention to cancers of many types. In general, the method will be employed with cancer types which are considered to be targets for Hsp27 therapy, including in particular those where there has been a previous determination of Hsp27 overexpression for the patient's cancer or where a selected treatment induces hHsp27 expression. Specific non-limiting examples of cancer types that may be treated using the method of the invention include breast, prostate, ovarian, uterine, non-small cell lung, bladder, gastric, liver, endometrial, laryngeal and colorectal cancers; squamous cell carcinomas such as esophageal squamous cell carcinoma, glioma, glioblastoma, melanoma, multiple myeloma and lymphoma.

In the combination therapy of the present invention, a second active agent is combined with an inhibitor of Hsp27. The second active agent is an inhibitor of EGFR tyrosinase kinase or an antifolate. The second active agent is selected to have independent therapeutic activity for the cancer to be treated in a particular individual.

Definitions

As used in the specification and claims of the present application, the term "treating" refers to performing the method steps of the invention with intention and expectation of a therapeutic benefit to the patient. It would be understood in the art that not all patients respond favorably, or to the same extent to a given treatment. Furthermore, it will be understood in the art that the results obtained for any individual cannot be compared to results for that individual in the absence of the treatment. Thus, actual therapeutic benefit is not required to fall within the scope of the concept of "treating" nor is conclusive evidence that an observed benefit arose from the treatment.

The term "Hsp27" refers to heat shock protein 27, an approximately 27 kilodalton stress-induced protein. Hsp27 is also sometimes referred to as heat shock protein beta-1 (HSPB1). The sequences of Hsp27 are known in the art for *Homo sapiens* (AB020027, X54079, NM_006308, NM_001540 and NM_001541), dogs (NP_001003295), cattle (NP_001020740), mice (NP_038588) and other species.

The term "EGFR" refers to epidermal growth factor receptor (EGFR). Its activated form, phosphorylated EGFR (pEGFR), is correlated with poor prognosis in lung cancer. Selvaggi G, Novello S, Torri V. et al. Ann Oncol. 2004 January; 15(1):28-32.

The term "NSCLC" refers to non-small cell lung cancer, a recognized subset of lung cancer.

The term "SCC" refers to squamous cell carcinoma. SCC can occur in lung tissue or in other locations in the body. SCC originating in lung tissue is a recognized subset of NSCLC The term "AD" or "lung AD" refers to lung adenocarcinoma, a different recognized subset of NSCLC.

The term "LCC" refers to large cell lung carcinoma, a different recognized subset of NSCLC.

The term "lung cancer" when used without further labeling refers generically to NSCLC, including lung SCC, lung-AD and LCC.

The term "p-Hsp27 (Ser82)" refers to hsp27 that is phosphorylated at serine 82. Other serine residues may also be phosphorylated as described in "Regulation of HSP27 function is highly dependent on phosphorylation (Stetler et al., 2009, 2010). In response to cellular stimuli, such as oxidative stress, Hsp27 is phosphorylated at several distinct serine residues (Ser15, Ser78, and Ser82 in humans). Phosphorylation at Ser82 leads to dissociation to lighter oligomers (Thériault et al., 2004) and loss of the chaperone function of HSP27 which is associated with the nonphosphorylated structure. p-Hsp27 can suppress cell death-signaling (Bruey et al., 2000; Concannon et al., 2001; Benn et al., 2002; Rane et al., 2003; Lee et al., 2005; Voss et al., 2007). Cell death suppression requires phosphorylation of Hsp27 (Benn et al., 2002). Thus, measurement of increased levels p-Hsp27 is an indication that Hsp27 is acting in a cytoprotective manner, while a decrease in p-Hsp27 in targeted cells is indicative of a therapeutic enhancement.

The term "PARP" refers to poly-(ADP-ribose) polymerase, a marker of apoptosis and a caspase substrate.

Caspase 3 refers to an enzyme that is a member of the cysteine-aspartic acid protease (caspase) family associated with the apoptotic pathway. Cleaved caspase 3 is the large fragment (17/19 kDa) of activated caspase-3 resulting from cleavage adjacent to Asp175. Antibodies are used that bind to cleaved caspase-3 but that do not recognize full length caspase-3 or other cleaved caspases. This antibody detects non-specific caspase substrates by Western blot.

The term siRNA refers to double stranded RNA or RNA and DNA species that are active to reduce expression of targeted gene. These molecules are known variously as "small interfering RNA", "short interfering RNA" or "silencing RNA." siRNA strands are usually 20-25 nucleotides long, although larger precursor molecules which are subject to cleavage in vivo to form the active species are within the scope of the term as used herein.

A549 cells: ATCC No. CCL-185™ is an epithelial lung carcinoma (Giard D J, et al. In vitro cultivation of human tumors: establishment of cell lines derived from a series of solid tumors. J. Natl. Cancer Inst. 51: 1417-1423, 1973.) A549 cells are representative of NSCLC without an activating mutation in the EGFR tyrosine kinase domain. Such cells are not considered clinically sensitive to EGFR-TKI such as erlotinib and gefitinib.

HCC827: ATCC No. CRL-2868™ is an epithelial cell line derived from lung adenocarcinoma. Growth and subculturing conditions are provided at www.atcc.org/ATCCAdvancedCatalogSearch/ProductDetails/tabid/452/Default.aspx?ATCCNum=CRL-2868&Template=cellBiology. HCC827 is representative of NSCLC (lung adenocarcinoma) with an activating mutation in the EGFR tyrosine kinase domain (E746-A750 deletion).

Methods

The method referred to herein as "CI" or "combination index" is a quantitative analysis based on a theorem proposed by Chou-Talalay in the 1980s (Chou T C, Talalay P A. J. Biol. Chem (1977) 252: 6438-42; Chou T C. Talalay P A. Eur. J. Biochem. (1981) 115:207-216). Software called CalcuSyn (Biosoft, Cambridge UK) is available and was used for these studies to quantify phenomena such as synergism and inhibition. The software performs multiple drug dose-effect calculations using the Median Effect methods described by T-C Chou and P. Talalay (Trends Pharmacol. Sci. 4, 450-454).

CI<1 indicates synergism
CI=1 indicates additive effect
CI>1 indicates antagonism TUNEL: "TdT-mediated dUTP-biotin nick end labeling (TUNEL) staining (1)". TUNEL staining relies on the ability of the enzyme terminal deoxynucleotidyl transferase to incorporate labeled dUTP into free 3'-hydroxyl termini generated by the fragmentation of genomic DNA into low molecular weight double-stranded DNA and high molecular weight single stranded DNA.

Western blots: To perform Westerns, cell lysates were prepared under non-denaturing conditions. Briefly, the cell lysates were to immunoprecipition, and subsequently immunoblotted using antibody and visualized via electrophoresis and autoradiogram.

Crystal Violet: Crystal violet (CV) is a triphenylmethane dye (4-[(4-dimethylaminophenyl)-phenyl-methyl]-N,N-dimethyl-aniline) also known as Gentian violet (or hexamethyl pararosaniline chloride). The CV assay is used to determine cell viability or to determine cell proliferation under different testing conditions (Davey, Hazel M.; Kell, Douglas B. Microbial Reviews (1996) 60: 4: 641-696).

Inhibitors of Hsp27

As used in the present application, the term "inhibitor of Hsp27" refers to a compound that reduces the activity of Hsp27, either by interaction with Hsp27 or its intended target, or through reduction in the amount of Hsp27 present in cells Inhibitors of Hsp27 expression of various different types are known in the art. Examples of inhibitors includes nucleotide compounds targeting Hsp27, peptide aptamers, flavonoid inhibitors of Hsp27, antibodies that interact with Hsp27, and interferon-γ which has been shown to down-regulate expression of Hsp27. The specific route of administration, the dosage level and the treatment frequency will depend on the nature of the active agent employed. In general, the therapeutic agent may be administered by intravenous, intraperitoneal, subcutaneous, topical or oral routes, or direct local tumor injection.

In accordance with some embodiments, the Hsp27 inhibitor is a nucleotide inhibitor. Examples of nucleotide inhibitors include antisense sequences, which may be full-length antisense (see Horman et al., Int. J. Cancer (1999) 82: 574-582), or shorter oligonucleotide sequences, having a length of 100 bases or less, for example 12 to 30 bases. Such antisense species are complementary to the target Hsp27 gene to an extent sufficient to achieve antisense inhibition in vivo, and may include degeneracy to take into account allelic variation. Specific oligonucleotide antisense inhibitors of Hsp27 are known in the art from US Patent Publications 2004/0127441 and 2009/0264502 which are incorporated herein by reference.

In specific embodiments, the Hsp27 inhibitor is OGX-427, an antisense oligonucleotide made by OncoGenex that is currently in clinical trials for treatment of various types of cancer. OGX-427 is a 4-12-4 2'-MOE gapmer oligonucleotide with phosphorothiolatedinternucleotide linkages which can be represented as (Seq. ID No. 1)
5'-<u>GGGA</u>MeCGMeCGGMeCGMeCTMeCGGMe<u>UMeCAMeU</u>-3' where G, A, MeC, and T represent the nucleosides 2'-deoxyguanosine, 2'-deoxyadenosine, 2'-deoxy-5-methylcytidine, and 2'-deoxythymidine, the underlined nucleosides denote 2'-O-methoxyethyl (2'-MOE) modifications of the nucleosides, and the internucleotide linkages are phosphothioate-diester, sodium salts.

In other embodiments, the nucleotide Hsp27 inhibitor is a double stranded RNA species (or precursor) that operates by an siRNA mechanism to reduce expression of Hsp27. Specific RNA species for this purpose are known from US Patent Publication 2004/0127441 and Chauhan, et al. (2003) Cancer Res. 63, 6174-6177. One specific siRNA inhibitor used in the examples below has the sequence GCU GCA AAA UCC GAU GAGA (Seq ID No. 2) and it is used with its complement to form the active double stranded inhibitor.

Peptide aptamers (Gilbert et al, Oncogene. 2011 Mar. 21. [Epub ahead of print]); and antibodies (Tezel and Wax, J. Neuroscience 10:3553-3562 (2000) that interact with Hsp27 are also known and could serve as inhibitors of Hsp27 in accordance with the invention. Other peptides that bind to Hsp27, such as CP91 or binding fragments thereof as described in US Patent Publication No. 2007/0003555 could also be employed.

Cytokines such as interferon-γ are also known to inhibit Hsp27 and can be used as inhibitors in the present invention. Yonekura et al., Cell Death and Differentiation (2003) 10: 313-322.

Other inhibitors of Hsp27 are also known which are generally "small molecule" inhibitors. These include flavonoids such as quercetin, (Morino et al., in vivo (1997) 11: 265-270; JP 10045572, JP 10045574, JP10036261 and JP 10036267), and biphenyl isooxazoles such as 5-(5-Ethyl-2-hydroxy-4-methoxyphenyl)-4-(4-methoxyphenyl)isoxazole (KRIBB3) (Shin et al. The Journal of Biological Chemistry VOL. 280, NO. 50, pp. 41439-41448, Dec. 16, 2005). KRIBB3 is available commercially from Sigma-Aldrich is understood to reduce Hsp27 activity by acting as a specific inhibitor (IC50 of 50 nM) of PKC-dependent phosphorylation of Hsp27. Related compounds are described in Lee et al., Bioorg Med Chem Lett. 2011 Feb. 1; 21(3):977-9. Epub 2010 Dec. 13. Berberine derivatives have also been shown to inhibit Hsp27. (EP 0 813 872) Paclitaxel has also been shown to be an inhibitor of Hsp27 expression. (Tanaka et al., Int J Gynecol Cancer. 2004 July-August; 14(4): 616-20). Nucleoside inhibitors such as brivudine also are within the scope of the invention.

Inhibitors of EGFR Tyrosine Kinase

As used in the present application, the term "inhibitor of EGFR tyrosine kinase" refers to inhibitors of the tyrosine kinase activity of epidermal growth factor receptor (EGFR), either by interaction with EGFR tyrosine kinase or its intended target, or through reduction in the amount of EGFR tyrosine kinase present in cells.

Examples of inhibitors of EGFR tyrosine kinase activity include known therapeutic compounds such as erlotinib (Tarceva™) and gefitinib (Iressa™) both of which are quinazoline compounds.; PKI-166; EGFR-specific and irreversible inhibitors, such as EKI-569; a PAN-HER (human EGF receptor family) reversible inhibitor, such as GW2016 (targets both EGFR and Her2/neu); and a PAN-HER irreversible inhibitor, such as CI-1033 (4-anilinoquinazoline).

EGFR-targeting antibodies and antibody fragments, and their use in treatment of cancer are known and include cetuximab (Erbitux™) and panitumumab (Vectibix™). Others are known from US Patent Publication No. 2011-0117110.

Oligonucleotide sequences (antisense, siRNA and the like) for inhibition of wild-type or mutant forms of EGFR are known from US Patent Publication No. 2012-0022132;

US Patent Publication No. 2009-0118208 and US Patent Publication No. 2003-0170891.

Antifolates

Antifolates are folate-analogue metabolic inhibitors. They may interfere with one or more of three enzymes involved in purine and pyrimidine synthesis—thymidylate synthase (TS), dihydrofolate reductase (DHFR), and glycinamide ribonucleotide formyltransferase (GARFT). Specific antifolates used in cancer therapy include methotrexate, pemetrexed, pralatrexate, and raltitrexed.

Combinations of Agents

Each of the inhibitors of Hsp27 may be used individually or in combination with one or more of the other inhibitors. Each of these inhibitors or combinations may be used with any second agent that is an inhibitor of EGFR tyrosine kinase activity or an antifolate, with the proviso that the second agent is selected for utility in the treatment of the particular cancer with which the individual treated is diagnosed. In addition, combinations within the scope of the invention may be further combined with additional therapeutics effective treated.

Formulation and Administration

The therapeutic agents of the invention are suitably formulated in one or more pharmaceutically acceptable carriers of a type consistent with the intended mode of administration and the specific Hsp27 and second agent. In general, the Hsp27 and second agents can be administered as an injectable liquid, an oral or aerosol composition, and may be administered systemically (for example intravenous, intramuscular, or oral) or regionally to an area harboring a cancer to be treated (for example intra-nasal, intra-tumoral, intra-tracheal, intra-pleural and topical).

Inhalation strategies for antisense therapeutics are known, for example from Karras et al, Drug Discovery Today: Therapeutic Strategies (2006) 3(3): 335-341 and Crosby et al, J Pharmacol. and Exp. Therapeutics., (2007) 321: 938-946. See also, US Patent Publication No. 2006/0003954. Other modes of regional administration to the lungs include intra-pleural injection and intra-tracheal administration.

In some embodiments of the invention, the Hsp27 inhibitor is an antisense oligonucleotide. Oligonucleotide therapeutics are commonly being tested at treatment levels of 1 to 500 mg/m2/day and preferred treatment levels are selected to balance toxicity with therapeutic benefit. Such levels are appropriate for use in the therapeutic combinations of the invention. One specific oligonucleotide product is "OGX-427" (Seq ID No. 2) which is currently provided to human patients at about 600 mg per patient in a 25 mg/mL concentration formulated as a mannitol-phosphate buffer solution (pH 7.4) for IV administration. OGX-427 dosing solutions are administered intravenously using an infusion pump. In some situations, the administration will be preceded or accompanied by administration of an antihistamine. Antisense oligonucleotides may also be administered in specific carrier, such as that described in US Patent Publication No. US 2009/0142413 A1.

Other components used in the therapeutic combinations are used at levels consistent with usages for other purposes. Lower levels may be possible because of the effectiveness of the combination, or where more than one inhibitor of a given type is included.

Treatable Cancers

Some treatment-naïve cancers have been found to express Hsp27. In addition, Hsp27 expression may arise as a response to treatment with chemotherapy or radiotherapy. The method and the therapeutic combination of the invention are applicable to the treatment of cancers that inherently or as a consequence of prior or concurrent chemotherapy or radiation treatments express Hsp27. Specific cancers include, without limitation, prostate, bladder, lung, breast, osteosarcoma, pancreatic, colon, testicular, colorectal, urothelial, renal cell, hepatocellular, leukemia, lymphoma, and ovarian cancer, melanoma, central nervous system malignancies, and squamous cell carcinoma.

In some embodiments of the invention, the cancer is a treatment-naïve cancer that expresses Hsp27 at a level that is greater to a statistically significant extent than the amount of expression of Hsp27 in non-cancerous cells of the same type as the cancer. Thus, by way of example only, the level of Hsp27 expression in prostate cancer cells would be compared to an average value for non-cancerous prostate tissue.

In some embodiments of the invention, the cancer is one that been previously treated in the individual by chemotherapy. In this case, the cancer is preferably one that expresses Hsp27 at a level that is greater to a statistically significant extent than the amount of expression of Hsp27 in non-cancerous cells of the same type as the cancer and/or that expresses Hsp27 as a level greater than levels in the individual prior to the treatment.

In some embodiments of the invention, the cancer is one that been previously treated in the individual by radiotherapy. In this case, the cancer is preferably one that that expresses Hsp27 at a level that is greater to a statistically significant extent than the amount of expression of Hsp27 in non-cancerous cells of the same type as the cancer and/or that expresses Hsp27 as a level greater than levels in the individual prior to the treatment.

In each of these embodiments, the therapeutic combination as described above can be used.

As shown further in the examples, specific cancers for which the invention is particularly useful are non-small cell lung cancers in some patients possessing an activating mutation in the EGFR gene, NSCLC can be treated using EGFR-TKIs such as erlotinib and gefitinib. However, almost without exception, these NSCLC patients develop acquired resistance to EGFR-TKIs as treatment proceeds, apparently as a result of the development of a second mutation. (Pao, W; Miller, VA; Politi, KA; Riely, GJ; Somwar, R; Zakowski, MF; et al. Acquired resistance of NSCLC to gefitinib or erlotinib is associated with a second mutation in the EGFR kinase domain. PLoS Med (2005);2:e73.) Treatment of A549 NSCLC cells with erlotinib induces Hsp27 expression and the knock down of this expression results in enhanced cytotoxic effect and apoptosis. (See, Experimental results, A and B, herein) Thus, for treatment of NSCLC, the combination therapy of the EGFR-TKI and the Hsp27 inhibitor provides two benefits: First , it enhances the initial activity of the EGFR-TKI so that more effectiveness will be obtained before the onset of resistance. Second, it maintains the efficacy of the drug for a longer period of time, even after the resistance causing mutations have begun to appear. Erlotinib induces also expression of Hsp27 in HCC827 cells which are representative of NSCLC (lung adenocarcinoma). (Experimental Results, G, herein). Suppression of Hsp27 results in enhanced efficacy of erlotinib in these cells. Greater levels of Hsp27 expression were observed in erlotinib resistant cell lines derived from HCC827 than in the parent strain. This may be drug resistance arising due to a second mutation in the EGFR thymidine kinase , reducing the sensitivity of the EGFR-TK to the drug, or may be a separate mechanism of drug resistance in which the cells produce higher levels of Hsp27. Regardless of mechanism, enhancement of drug activity continues in cancers that develop resistance to erlotinib. (See Experimental results, J, herein).

Beneficial Effects of the Invention

Compounds such as inhibitors of EGFR tyrosine kinase activity and antifolates are effective as chemotherapy agents because they disrupt important metabolic functions of the living cells and they can therefore have substantial detrimental side effects. While these side effects are tolerable to some extent because of the seriousness of the condition being treated (cancer), reduction in side effects is always desirable and the dosage used often reflects a balancing between these two competing interests. The present invention permits the usage of substantially lower dosages of the second agent with the same degree of efficacy. Since Hsp27 inhibitors can have low toxicity (for example OGX-427 (Seq. ID No. 1) was found to have no dose-limiting toxicity in a Phase I clinical study of patients with castrate resistant prostate cancer, breast cancer, ovarian cancer or non-small cell lung cancer), this means that patients can receive comparable therapeutic effect with fewer side effects, or greater therapeutic benefit from a high dose with the same level of side effects.

Furthermore, while both Hsp27 inhibitors and the second agent have individual beneficial activity, the combined benefit was synergistic at least at some dosage levels. Thus, the result of the invention is not merely the additive effect of two known therapeutics.

Experimental Results

A. Erlotinib Induces Expression of Hsp27

Experimental results showed that erlotinib induces Hsp27 expression in A549 lung cancer cells. A549 lung cancer cells were exposed to 10 µM Erlotinib and the amount of p-Hsp27 (ser82), Hsp27, p-EGFR (Tyr 1068), EGFR, cleaved PARP (an indicator of apoptosis) were determined by Western Blot after 1, 6, 24. 48 and 72 hours of exposure. Increasing amounts of EGFR, Hsp27 and p-Hsp27 were observed over time. p-EGFR was initially present but was not observed following treatment. Cleaved PARP was observed at all times following 24 hours of treatment.

The experiment was repeated using 48 hours of treatment time and erlotinib at levels of 2.5, 5 and 10 µM. Qualitatively similar results were observed at all concentration.

Finally cells were treated with 5 or 10 M Erlotinib for 24 or 48 hours. Hsp27 mRNA expression was analyzed by quantitative RT-PCR. Hsp27 mRNA levels were normalized to levels of GAPDH mRNA. Bars, SD. ** and *, differ from control ($P<0.01$ and $P<0.05$, respectively). The results are shown in FIG. 1. As indicated, both levels of erlotinib resulted in increased Hsp27 expression.

B. Hsp27 Knockdown Enhances Erlotonib Effectiveness

Figure 2:
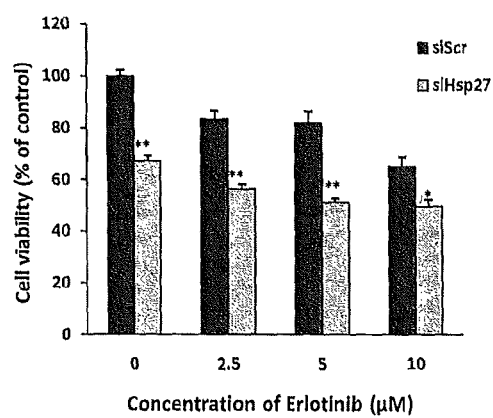
FIG. 2 shows cell viability as a function of erlotinib treatment with and without treatment with siHsp27.

It was also shown that Hsp27 knockdown enhances cytotoxic effect and apoptosis after treatment with erlotinib. Cells were transfected with 20 nM Hsp27 siRNA (Seq ID No. 2) or a scrambled siRNA duplex containing 5'-CA-GCGCUGACAACAGUUUCAU-3' SEQ ID NO: 3 for 1 day, and treated with varying concentrations of erlotinib for 48 hours. Cell viability was determined by crystal violet assay. The results are summarized in FIG. 2. As shown, at each concentration, the reduction in cell viability was greater when both agents were present. The use of the combination decreased cell viability with 2.5 µM erlotinib more that erlotinib alone at 4 times the concentration.

Protein expression was also analyzed after 48 hours exposure to 10 µM erlotinib. Hsp27 and p-Hsp27 were both absent in cells treated with the siHsp27 but not the scrambled control. P-EGFR was lower in cells treated with the combination that in cells treated with siHsp27 alone. Cleaved PARP was greater in cells with the combined treatment than in cells with either treatment alone.

Figure 3A:
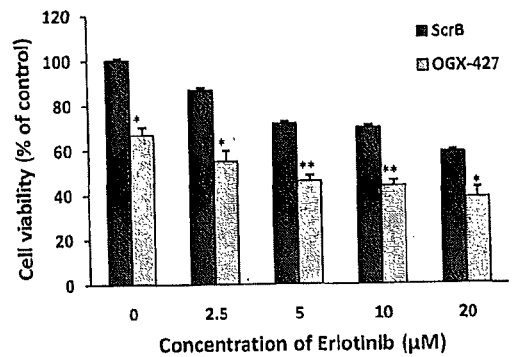
FIG. 3A shows cell viability as a function of erlotinib treatment with and without treatment with Hsp27 antisense.
Figure 3B:
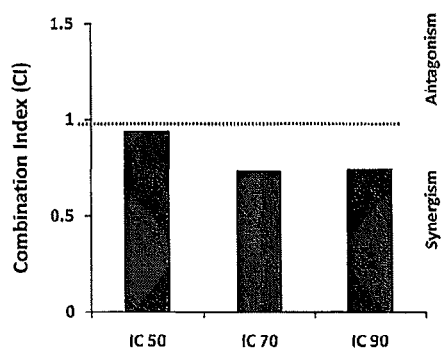
FIG. 3B shows the combination index indicative of synergy for the combined treatment of erlotinib and Hsp27 antisense.
Figure 3C:
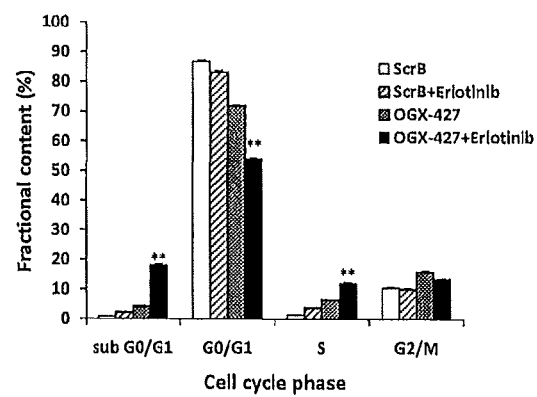
FIG. 3C shows cell cycle results for treatments with erlotinib and Hsp27 antisense.

Combined treatment of A549 cells with OGX-427 (Seq ID No. 1) and erlotinib was found to be synergistic. A549 cells were transfected with 50 nM OGX-427 (Seq. ID No. 1) or a scrambled control on two consecutive days and then treated with 10 µM erlotinib for 72 hours after the second transfection. Cell viability was determined using a crystal violet assay. The results are shown in FIG. 3 A.

The synergistic effect of combination treatment with Erlotinib and OGX-427 in vitro was assessed using combination index (CI) values calculated by CalcuSyn software were assessed in A549 cells treated for 72 hours with OGX-427 alone, Erlotinib alone or combined treatment. The CI for inhibitory concentration (IC) 50, IC75 and IC90 was 0.9, 0.7 and 0.7, respectively, indicative of a synergistic effect of this combined treatment at all levels of erlotinib tested (See FIG. 3B).

To evaluate the apoptotic rate after combination treatment with Erlotinib and OGX-427, cells were treated as with described above. Protein expression was analyzed by western blotting. Cleaved caspase-3 and cleaved PARP were elevated in cells with the combined treated, while p-EGFR, Hsp27 and p-Hsp27 were reduced. Flow cytometry was used to quantify the percentage of cells in each cell cycle phase. (FIG. 3C; Bars, SD. **, differ from ScrB ($P<0.01$).)

Figure 4A:
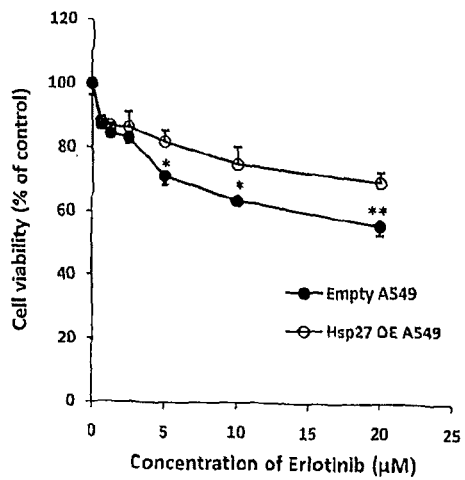
FIG. 4A shows cell viability in A549 cells overexpressing Hsp27 following erlotinib treatment.

C. Hsp27-Overexpression Protects from Cell Death Induced by Erlotinib in A549 Cells A547 cells overexpressing Hsp27 (Hsp27 OE A549) cells were established and protein expression was confirmed by western blotting. The effect of overexpression of Hsp27 protein on the sensitivity to Erlotinib in A549 cells was tested using the. Hsp27 OE A549 cells and control vector-transfected (Empty A549) cells were treated with the indicated concentration of Erlotinib for 72 hours. The cell viability was determined by crystal violet assay. FIG. 4A (Bars, SD. ** and *, differ from Empty A549 ($P<0.01$ and $P<0.05$, respectively).

Figure 4B:
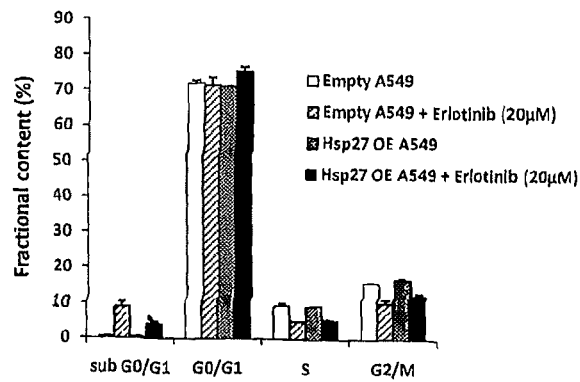
FIGS. 4B and C show flow cytometry results for A549 cells overexpressing Hsp27 following erlotinib treatment.
Figure 4C:
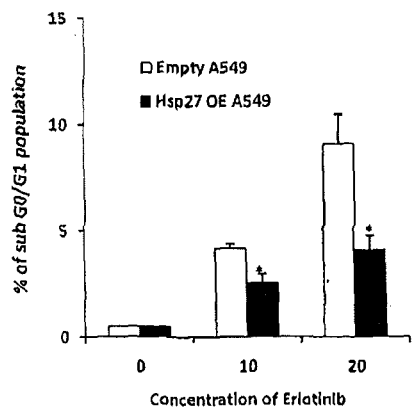

A decreased apoptotic rate after Erlotinib treatment in cells with Hsp27 overexpression was also observed. Hsp27 OE A549 and Empty A549 cells were treated with varying levels of erlotinib. Protein levels were analyzed by western blotting and higher levels of cleaved PARP were observed in the empty A549 cells. The cells undergoing apoptosis (subG0/G1 fraction) were quantified using flow cytometry. FIGS. 4B and C. (Bars, SD. *, differ from Empty A549 ($P<0.05$)).

D. Hsp27-Overexpression Protects from Cell Death Induced by Erlotinib in A549 Cells Western blotting technique was used to assess relative levels of certain proteins in A549 and A549 over-expressing (OE) cell lines cultured in the present of erlotinib at concentrations of 0 to 20 micromolar after 72 hours. Cleaved PARP, p-EGFR(Tyr1068), EGFR, p-Hsp27(Ser82), Hsp27, and Beta-actin were assayed. A decrease in p-EGFR (Tyr1068) in the presence of erlotinib for both cell lines, and a dose-dependent increase in p-Hsp27(Ser82) in the A549 OE cell line were observed. Cleaved PARP increased in both cell lines as doses of erlotinib increased, indicating an increase in apoptosis.

Figure 5A:
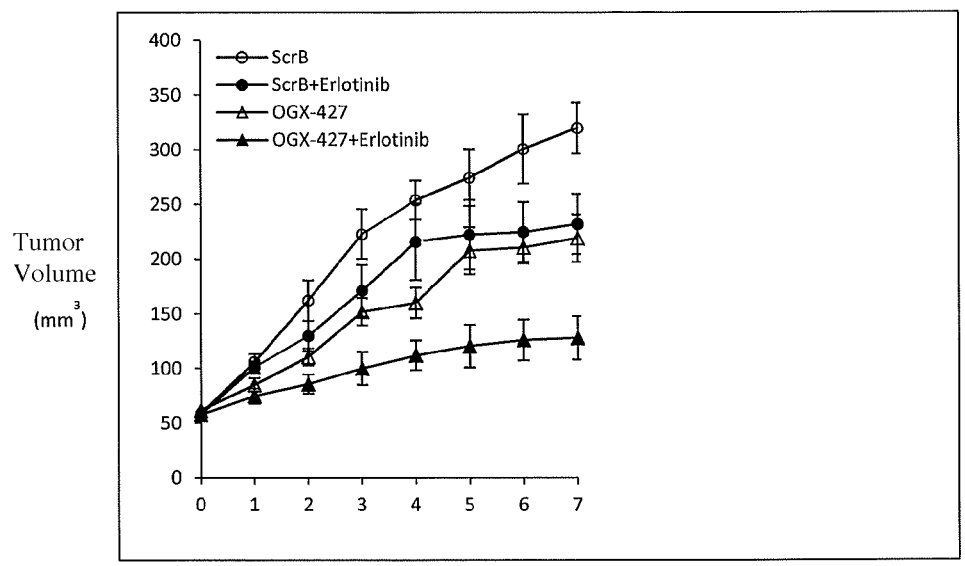
FIG. 5A shows change in tumor volume in A549 xenograft tumors over time with various treatments.
Figure 5B:
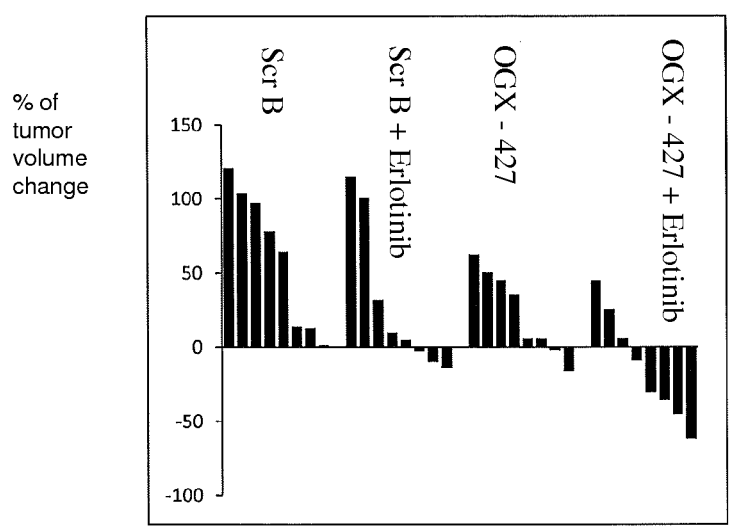
FIG. 5B shows this data in bar graph form.

The in vitro results were confirmed using an in vivo test on A549 xenograft tumors. A549 cells were inoculated s.c. and when tumors reached 50-100 mm3, mice were treated with ScrB control oligodeoxynucleotide (ScrB)+diluent, ScrB+Erlotinib, OGX-427+diluent or OGX-427+Erlotinib Tumor volume was monitored for 7 weeks after treatment. As shown in FIG. 5A, the combined treatment substantially reduced tumor growth as compared to either treatment individually. Each data point represents the mean tumor volume in each group containing 8 mice±SEM. *, differ from ScrB+diluent, ScrB+Erlotinib or OGX-427+diluent treatment group (P<0.05). B, tumors were collected after 49 days. Hsp27, ph-Hsp27 (Ser82), EGFR, p-EGFR, Ki-67 and TUNEL were evaluated by immunohistochemical analysis (original magnification: ×200). A bar graph recapitulating this same information illustrates the percent of volume change showing the greatest effects when erlotinib and OGX-427 were used together (FIG. 5 B). In each cluster, the 8 lines represent the % tumor volume change on the $1^{st}$ through $8^{th}$ days. As can be seen, tumor size begins to decrease earlier in the combined OGX-427 and erlotinib treatment.

After the seven week treatment, mice were sacrificed and tumors excised for assessment. Tissue preparations were subjected to TUNEL staining, and the results are shown in FIG. 5C More signs of apoptosis were observed for OGX-427 and erlotinib combined than any of the other three groups.

E. Pemetrexed Induces Hsp27 Expression

Experimental results showed that Hsp27 is induced in A549 cells. A549 cells were cultured as previously described by others (Van Schaeybroeck, Sandra; Kyula, Joan; Kelly, Donal M; et al. Mol Cancer Ther (2006) 5; 1154), and treated with pemetrexed at a concentration of 0, 0.25, 0.5, and 1.0 microMoles for a 48 hour period. Western gels were run on cell protein prepared under standard non-denaturing conditions, and relative levels of p-Hsp27 (Ser82), Hsp27, cleaved PARP, and beta-actin were detected using commercial antibodies from Cell Signalling (Danvers, USA). Protein levels from zero to 48 hours for a 1 microMolar pemetrexed exposure were measured. The signals for pHsp27 and cleaved PARP increase with dose and are greatest at 48 hours, providing evidence that apoptosis and Hsp27 activation are increased in the presence of pemetrexed.

The dose effect of pemetrexed at concentrations of from 0 to 1 micromole was measured on the same proteins as assayed in the above time course experiment. pHsp27 and cleaved PARP levels show similar patterns.

F. Hsp27 Knockdown Enhances Pemetrexed Effectiveness

OGX-427 was also shown to enhance the antitumor effect of premetrexed in A549 cells. A549 cells were treated 50 nM OGX-427 on 2 consecutive days and incubated with varying concentrations of Pemetrexed for 72 h. 72 h later, cell viability was determined by crystal violet assay. The results are shown in FIG. 6. (** p<0.01) Reduction in cell viability comparable to 1 µM pemetrexed alone were obtained using the combination therapy and only 0.1 µM, a ten-fold reduction. Protein levels were also determined in these cells by immunoblotting. Increased cleaved PARP was observed, indicating that the Hsp27 inhibitor increases apoptotic rates as compared to pemetrexed alone.

G. Hsp27 is Overexpressed in NSCLC of Different Subtypes

Distribution of Hsp27 positive and negative cells (n=440) was assessed in a variety of human lung cancer tissues, namely squamous cell lung carcinoma (SCC), lung adenocarcinoma (AD), and large-cell lung carcinoma (LCC). Assays for Hsp27 and p-Hsp27 are available commercially from Cell Signalling, Danvers USA, and Perkin-Elmer (USA).

| Tumor Type | Positive Cells | Detected Signal |
|---|---|---|
| SCC (n = 214) | 82.2% (176) | Hsp27 |
| AD (n = 195) | 71.3% (139) | Hsp27 |
| LCC (n = 31) | 67.7% (21) | Hsp27 |
| SCC (n = 212) | 86.8% (184) | p-Hsp27 (Ser 82) |
| AD (n = 184) | 79.9% (147) | p-Hsp27 (Ser 82) |
| LCC (n = 31) | 87.1% (27) | p-Hsp27 (Ser 82) |

Thus, the reduction in Hsp27 generally and in combination with a second agent used in the treatment of particular types of lung cancer is beneficial in a majority of human NSCLC patients.

H. Erlotinib Induces Hsp27 in HCC827 Cells

Lung cancer cell line HCC827 was cultured and exposed, under otherwise normal conditions, to from 0 to 50 micromolar erlotinib, and the cells were lysed under non-denaturing conditions and protein content was subjected to Western blotting technique.

Figure 7:
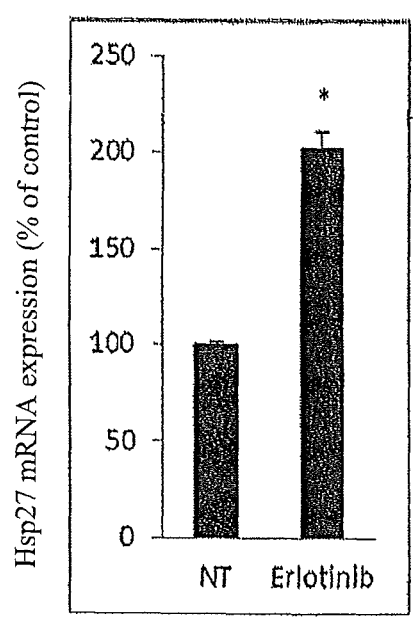
FIG. 7 shows expression of Hsp27 in HCC827 lung cancer cells with and without treatment with erlotinib.

In HCC827cells, erlotinib at 2.5 nanomolar concentration generated a decrease in p-EGFR (Tyr068) and an increase in p-Hsp27(ser82) as compared to non-treated cells, while protein levels for P-Hsp27(ser82), Hsp27 were increased. The increase is in Hsp27 is shown graphically in FIG. 7.

Figure 8A:
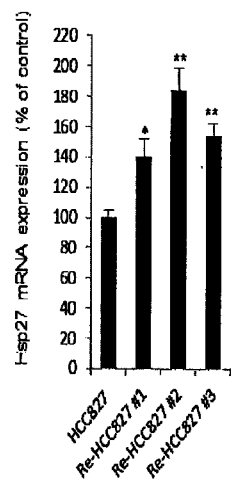
FIG. 8A shows Hsp27 mRNA expression in parental and erlotinib resistant HCC827 cells.
Figure 8B:
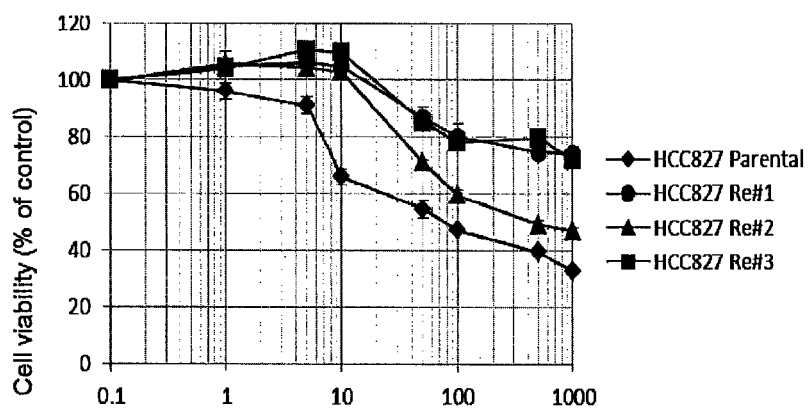
FIG. 8B shows cell viability as a function of erlotinib concentration in parental and erlotinib resistant HCC827 cells.

I. Overexpression of Hsp27 in HCC827 Cell Line Coincides with Resistance to Erlotinib Erlonitib-resistant HCC827 cells (Re-HCC827 #1,-#2, and -#3) were established by exposure to erlotinib and protein expression was confirmed by Western blotting. The three new cell lines were resistant to erlotinib treatment and overexpressed Hsp27 (FIG. 8A), and had elevated levels of p-Hsp27 as compared to the parent cell lines. The graph in FIG. 8 B shows cell viability for the parental HCC827 cell line and the three resistant derivations (Re#1, #2, and #3) under conditions of increasing concentrations of erlotinib (0.1 to 1000 nanoMole). The resistant cell lines are able to overcome the effects of erlotinib to a greater degree than the parental cell line can.

Figure 9A:
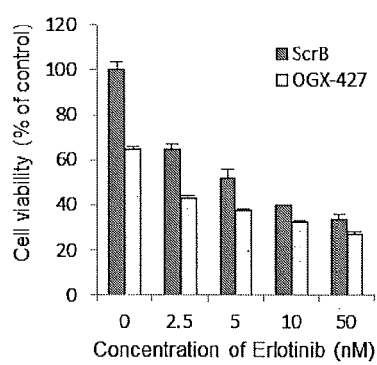
FIG. 9A shows cell viability of parental HCC827 cells at different concentrations of erlotinib, with and without treatment with OGX-427.
Figure 9B:
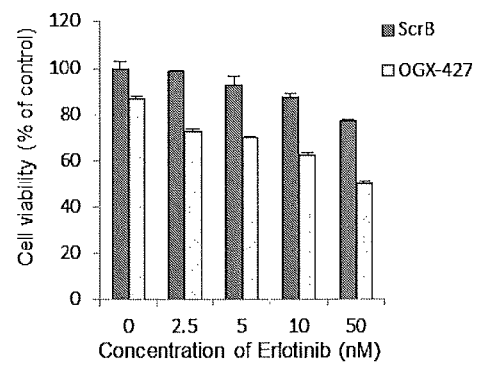
FIG. 9B shows cell viability of erlotinib resistant HCC827 cells at different concentrations of erlotinib, with and without treatment with OGX-427.

J. Hsp27 Suppression Sensitizes Both HCC827 Parental and Resistant Cells to Erlotinib Two lung cancer cell lines, HCC827 parental and resistant (HCC827 #3) were cultured according to supplier's directions in RPMI 1640 and 10% FCS. OGX-427 was added to HCC827 and Re-HCC827 #3 cell cultures in the presence of increasing doses of erlotinib (0, 2.5, 5, 10 and 50 nM). ScrB control oligodeoxynucleotide was used as a control for the OGX-427. Cell viability was measured using crystal violet technique. The results were expressed as a percentage of the cell viability in the presence of Oligofectamine™ control in FIGS. 9A and 9B for the parental and resistant cell lines respectively. The second, paler bars in the graphs are the OGX-427 treated cells, while the darker bars represent the cell viability of cells treated with ScrB control oligodeoxynucleotide.

Western blotting technique was used to assess the mechanisms of sensitization for both the parental and resistant HCC827 cell lines, under four conditions: ScrB control oligodeoxynucleotide only, ScrB control oligodeoxynucleotide with erlotinib, OGX-427 alone, and OGX-427 with erlotinib. Levels of p-EGFR(Tyr1068), EGFR, Hsp27, Cleaved PARP, Cleaved and whole Caspase-3, and beta-actin (cell protein control) were detected. Similar results were observed for both parental and resistant cell lines treated with both OGX-427 and erlotinib, with decreases in p-EGFR (Tyr1068) and Hsp27 as compared to non-treated cells, while protein levels for cleaved Parp and cleaved caspase-3 were increased.

K. Hsp27 Suppression Sensitizes A549 Mock and OE to Erlotinib

A Western blot was performed on A549 cells treated with ScrB control oligodeoxynucleotide, ScrB control oligodeoxynucleotide with erlotinib, OGX-427 alone, and OGX-427 with erlotinib. Western blotting technique was used to assay levels of P-EGFR(Typr1068), EGFR, p-Hsp27 (Ser82), HSP27, cleaved PARP, cleaved and whole Caspase-3, and beta-actin. Cleaved PARP and cleaved Caspase-3 levels were highest under the influence of the OGX-427 and erlotinib combination, suggesting that the apoptotic effect was greatest under those conditions.

L. Hsp27 Suppression with Pemetrexed Treatment

The synergistic effect of combination treatment with pemetrexed and OGX-427 was assessed in A549 cells. Cells were treated with ScrB control oligodeoxynucleotide, OGX-427 alone, pemetrexed with ASO control, and OGX-427 and pemetrexed together. An additional control was Oligofectamine™ transfecting agent alone. The cells were treated with OGX-427 for 2 consecutive days, and then incubated with pemetrexed for 72 hours. Another 72 hours later, cell viability was determined by crystal violet assay. The relative amounts of OGX-427 and pemetrexed was maintaed constant as the total amount of treatment agent was increased. The concentrations were:

| Test Compounds | Concentrations | | | | |
|---|---|---|---|---|---|
| OGX-427 nM | 0 | 12.5 | 25 | 50 | 100 |
| Pemetrexed (microM) | 0 | 0.25 | 0.5 | 1.0 | 2.0 |

Figure 10A:
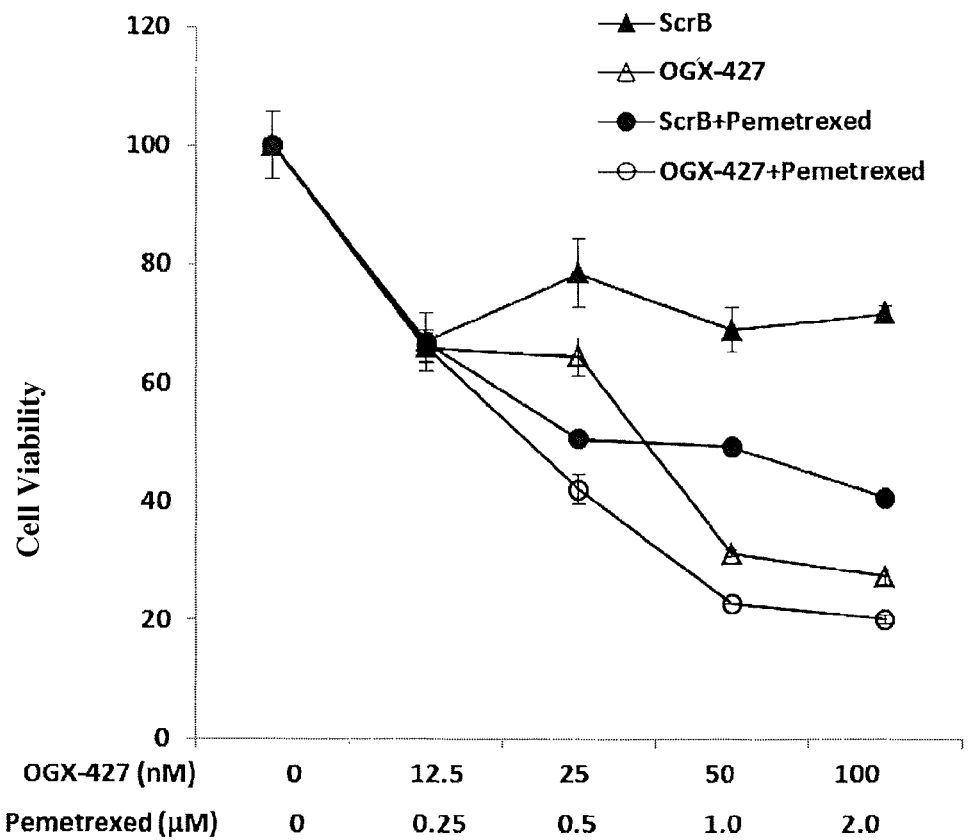
FIG. 10A shows cell viability for individual and combination therapies using pemetrexed and OGX-427 at increasing concentrations of therapeutic.

The results are summarized in FIG. 10A. As shown, cell viability after was lowest in the cell to which combined OGX-427 and erlotinib treatment was applied.

Figure 10B:
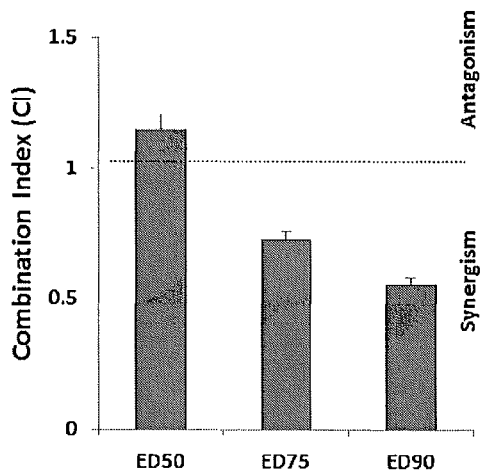
FIG. 10B is a combination index (CI) plot of this data.

When the values were graphed using combination index (CI) values calculated by CalcuSyn™ software. The combination index (CI) for effective concentrations (EC) ED75 and ED90 were indicative of a synergistic effect of this combined treatment (See FIG. 10B).

All of the publications referred to herein are incorporated herein by reference in their entirety.

The invention claimed is:

1. A method for treating lung cancer in an individual, consisting of the steps of
administering to the individual suffering from lung cancer a therapeutically effective amount of a first active agent which is an oligonucleotide inhibitor of Hsp27 activity, wherein the first agent is OGX-427 (SEQ ID NO: 1), and
administering to the individual an amount of erlotinib, wherein the first agent is administered before the second agent.

2. The method of claim 1, wherein the individual is human.

* * * * *